US010335242B2

(12) United States Patent
Devengenzo et al.

(10) Patent No.: US 10,335,242 B2
(45) Date of Patent: Jul. 2, 2019

(54) INDICATOR FOR TOOL STATE AND COMMUNICATION IN MULTI-ARM ROBOTIC TELESURGERY

(71) Applicant: INTUITIVE SURGICAL OPERATIONS, INC., Sunnyvale, CA (US)

(72) Inventors: Roman L. Devengenzo, San Jose, CA (US); David S. Mintz, Mountain View, CA (US); Tracey A. Morley, Sunnyvale, CA (US); Theodore C. Walker, Portola Valley, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 469 days.

(21) Appl. No.: 14/542,126

(22) Filed: Nov. 14, 2014

(65) Prior Publication Data
US 2015/0073437 A1 Mar. 12, 2015

Related U.S. Application Data

(63) Continuation of application No. 13/599,336, filed on Aug. 30, 2012, now Pat. No. 8,894,634, which is a
(Continued)

(51) Int. Cl.
*A61B 34/00* (2016.01)
*A61B 34/30* (2016.01)
(Continued)

(52) U.S. Cl.
CPC .............. *A61B 34/70* (2016.02); *A61B 34/30* (2016.02); *A61B 34/37* (2016.02); *A61B 90/361* (2016.02);
(Continued)

(58) Field of Classification Search
CPC ......... A61B 34/30; A61B 34/35; A61B 34/37; A61B 34/70; A61B 2090/0807;
(Continued)

(56) References Cited

U.S. PATENT DOCUMENTS

| 4,281,447 A | 8/1981 | Miller et al. |
| 4,332,066 A | 6/1982 | Hailey et al. |

(Continued)

FOREIGN PATENT DOCUMENTS

| EP | 1462895 A1 | 9/2004 |
| GB | 2350696 A | 12/2000 |

(Continued)

OTHER PUBLICATIONS

Chinese Patent Application No. 200680022931.5 Office Action dated Jul. 20, 2011, 8 pages.
(Continued)

*Primary Examiner* — Ahmed M Farah
(74) *Attorney, Agent, or Firm* — Haynes and Boone, LLP

(57) ABSTRACT

A method comprises receiving an input at a control system indicating a status change for a first tool coupled to a first manipulator assembly of a telesurgical system. The status change is correlated to a procedure to decouple the first tool from the first manipulator assembly or manually reconfigure the first manipulator assembly. The method also includes transmitting a command to the first manipulator assembly. Responsive to the transmitted command, a multiple-color light emitting diode array in an indicator section on the first manipulator assembly is activated to generate a signal indicating a reconfiguration action for the first tool or the first manipulator assembly to a first user.

19 Claims, 12 Drawing Sheets

Related U.S. Application Data continuation of application No. 11/556,484, filed on Nov. 3, 2006, now Pat. No. 8,273,076, which is a continuation-in-part of application No. 11/478,416, filed on Jun. 28, 2006, now Pat. No. 8,100,133.

(60) Provisional application No. 60/752,755, filed on Dec. 20, 2005, provisional application No. 60/695,611, filed on Jun. 30, 2005.

(51) Int. Cl.
*A61B 34/37* (2016.01)
*A61B 17/00* (2006.01)
*A61B 90/00* (2016.01)

(52) U.S. Cl.
CPC ............ *A61B 2017/00115* (2013.01); *A61B 2017/00477* (2013.01); *A61B 2017/00482* (2013.01); *A61B 2017/00734* (2013.01); *A61B 2034/305* (2016.02); *A61B 2090/0807* (2016.02); *A61B 2560/04* (2013.01)

(58) Field of Classification Search
CPC .... A61B 2090/0808; A61B 2090/0811; A61B 90/10; A61B 90/11; A61B 90/13; A61B 90/20; A61B 17/00; A61B 2017/00017; A61B 2017/00057; A61B 2017/00115; A61B 2017/00128; A61B 2017/00234; A61B 2017/00477; A61B 2017/00482; A61B 2017/00486
USPC ........ 606/1, 10–52, 130; 74/490.01, 490.07; 901/30, 31, 36, 41; 340/572.1
See application file for complete search history.

(56) References Cited

U.S. PATENT DOCUMENTS

| | | |
|---|---|---|
| 4,486,928 A | 12/1984 | Tucker et al. |
| 4,500,065 A | 2/1985 | Hennekes et al. |
| 4,512,709 A | 4/1985 | Hennekes et al. |
| 4,706,372 A | 11/1987 | Ferrero et al. |
| 4,710,093 A | 12/1987 | Zimmer et al. |
| 4,793,053 A | 12/1988 | Zuccaro et al. |
| 4,809,747 A | 3/1989 | Choly et al. |
| 4,830,569 A | 5/1989 | Jannborg |
| 4,832,198 A | 5/1989 | Alikhan |
| 4,943,939 A | 7/1990 | Hoover |
| 4,979,949 A * | 12/1990 | Matsen, III ............ A61B 17/15 414/9 |
| 4,996,975 A | 3/1991 | Nakamura |
| 5,018,266 A | 5/1991 | Hutchinson et al. |
| 5,078,140 A | 1/1992 | Kwoh |
| 5,143,453 A | 9/1992 | Weynant Nee Girones |
| 5,154,717 A | 10/1992 | Matsen, III et al. |
| 5,174,300 A | 12/1992 | Bales et al. |
| 5,217,003 A | 6/1993 | Wilk |
| 5,221,283 A | 6/1993 | Chang |
| 5,236,432 A | 8/1993 | Matsen, III et al. |
| 5,255,429 A | 10/1993 | Nishi et al. |
| 5,257,998 A | 11/1993 | Ota et al. |
| 5,271,384 A | 12/1993 | McEwen et al. |
| 5,294,209 A | 3/1994 | Naka et al. |
| 5,305,203 A | 4/1994 | Raab |
| 5,312,212 A | 5/1994 | Naumec |
| 5,313,935 A | 5/1994 | Kortenbach et al. |
| 5,343,385 A | 8/1994 | Joskowicz et al. |
| 5,354,314 A | 10/1994 | Hardy et al. |
| 5,355,743 A | 10/1994 | Tesar |
| 5,359,993 A | 11/1994 | Slater et al. |
| 5,372,147 A | 12/1994 | Lathrop, Jr. et al. |
| 5,397,323 A | 3/1995 | Taylor et al. |
| 5,399,951 A | 3/1995 | Lavallee et al. |
| 5,400,267 A | 3/1995 | Denen et al. |
| 5,402,801 A | 4/1995 | Taylor |
| 5,403,319 A | 4/1995 | Matsen, III et al. |
| 5,417,210 A | 5/1995 | Funda et al. |
| 5,427,097 A | 6/1995 | Depp |
| 5,451,368 A | 9/1995 | Jacob |
| 5,649,956 A | 7/1997 | Jensen et al. |
| 5,697,939 A | 12/1997 | Kubota et al. |
| 5,762,458 A | 6/1998 | Wang et al. |
| 5,784,542 A | 7/1998 | Ohm et al. |
| 5,792,135 A | 8/1998 | Madhani et al. |
| 5,800,423 A | 9/1998 | Jensen |
| 6,071,281 A | 6/2000 | Burnside et al. |
| 6,132,368 A | 10/2000 | Cooper |
| 6,223,100 B1 | 4/2001 | Green |
| 6,246,200 B1 | 6/2001 | Blumenkranz et al. |
| 6,331,181 B1 | 12/2001 | Tierney et al. |
| 6,522,906 B1 | 2/2003 | Salisbury, Jr. et al. |
| 6,574,355 B2 | 6/2003 | Green |
| 6,659,939 B2 | 12/2003 | Moll et al. |
| 6,731,988 B1 * | 5/2004 | Green .................... A61B 34/77 348/E13.014 |
| 7,024,750 B2 | 4/2006 | Isokyto et al. |
| 7,048,745 B2 | 5/2006 | Tierney et al. |
| 7,107,090 B2 | 9/2006 | Salisbury et al. |
| 7,525,274 B2 | 4/2009 | Kazi et al. |
| 7,643,862 B2 | 1/2010 | Schoenefeld |
| 7,666,191 B2 | 2/2010 | Orban, III et al. |
| 7,699,855 B2 | 4/2010 | Anderson et al. |
| 7,727,244 B2 | 6/2010 | Orban, III et al. |
| 7,763,015 B2 | 7/2010 | Cooper et al. |
| 7,896,815 B2 | 3/2011 | Thrope et al. |
| 7,955,322 B2 | 6/2011 | Devengenzo et al. |
| 8,100,133 B2 * | 1/2012 | Mintz ................... B25J 9/0084 128/898 |
| 8,182,470 B2 | 5/2012 | Devengenzo et al. |
| 8,273,076 B2 | 9/2012 | Devengenzo et al. |
| 8,527,094 B2 * | 9/2013 | Kumar ................... A61B 34/37 600/101 |
| 8,894,634 B2 | 11/2014 | Devengenzo et al. |
| 9,259,276 B2 | 2/2016 | Mintz et al. |
| 2003/0109780 A1 | 6/2003 | Coste-Maniere et al. |
| 2004/0106916 A1 * | 6/2004 | Quaid .................... A61B 34/71 606/1 |
| 2004/0267254 A1 | 12/2004 | Manzo et al. |
| 2005/0200324 A1 * | 9/2005 | Guthart .................... A61B 8/12 318/568.11 |
| 2006/0052684 A1 | 3/2006 | Takahashi et al. |
| 2006/0178559 A1 | 8/2006 | Kumar et al. |
| 2006/0235436 A1 * | 10/2006 | Anderson ............... A61B 34/71 606/130 |
| 2007/0073137 A1 * | 3/2007 | Schoenefeld .......... A61B 90/36 600/407 |
| 2007/0142969 A1 | 6/2007 | Devengenzo et al. |
| 2012/0059390 A1 | 3/2012 | Mintz et al. |
| 2016/0157943 A1 | 6/2016 | Mintz et al. |

FOREIGN PATENT DOCUMENTS

| | | |
|---|---|---|
| JP | 7024750 A2 | 1/1995 |
| JP | 07194610 A | 8/1995 |
| JP | 2003339736 A | 12/2003 |
| JP | 2005536314 A | 12/2005 |
| WO | WO-9313916 A1 | 7/1993 |
| WO | WO-199426167 | 11/1994 |
| WO | WO-9516396 A1 | 6/1995 |
| WO | WO-9530964 A1 | 11/1995 |
| WO | WO-9639944 A1 | 12/1996 |
| WO | WO-03094768 A1 | 11/2003 |
| WO | WO-2007005555 A2 | 1/2007 |

OTHER PUBLICATIONS

Chinese Patent Application No. 200680022931.5 Office Action dated May 10, 2010, 8 pages.
Chinese Patent Application No. 200680022931.5 Office Action dated Oct. 25, 2010, 7 pages.
Co-pending U.S. Appl. No. 60/752,755, filed Dec. 20, 2005.

(56) References Cited

OTHER PUBLICATIONS

Japanese Appl. No. 2008-519585 Office Action dated Sep. 26, 2011, 7 pages, including English translation.
PCT/US06/25465 International Search Report and Written Opinion of the International Search Authority, dated Apr. 3, 2007, 12 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP18162150.9 dated Oct. 5, 2018, 6 pages.
Extended European Search Report for Application No. EP18162151.7 dated Oct. 4, 2018, 8 pages.

* cited by examiner

MANIPULATOR UI-PROPOSAL
0=OFF, 1=RED, 2=GREEN, 3=DIM BLUE, 4=YELLOW, 5=BLUE, 6=PURPLE, 7=WHITE, 8=DIM PURPLE

| MODE | LED'S | NOTES |
|---|---|---|
| | CHANGE TO ISO 8583 FOR AESTHETICS DOES NOT INFRINGE ON UL | ANY UI STATUS ASSOCIATED WITH ARM IS INDICATED BY LED SEPARATES ARM IDENTIFICATION AND STATUS<br>ARMS: 1, 2, 3, C, OR COLORED LABELS<br>= RED/GREEN/YELLOW/WHITE<br>PHASED FEEL<br>BLUE IS DOMINANT COLOR FOR AESTHETICS<br>YELLOW = REFERENCE MONITOR FOR PROBLEM EXPLANATION<br>• REINFORCE WITH FAST BLINK RATE  RED=ERROR<br>• REINFORCE WITH FAST BLINK RATE  7 COLORS |
| NO STERILE ADAPTER PRESENT | OFF | |
| REMOVE INSTRUMENT FOR HOMING | BLINK F YELLOW/OFF | |
| STERILE ADAPTER ENGAGEMENT DELAY | WHITE | |
| STERILE ADAPTER ENGAGED/READY FOR TOOL ENGAGEMENT | WHITE | |
| INVALID STERILE ADAPTER | BLINK F YELLOW/OFF | |
| INSTRUMENT ENGAGEMENT DELAY | BLINK M DIM BLUE/WHITE | |
| GOOD INSTRUMENT<br>• GOOD INSTRUMENT; X LIVES LEFT<br>• INSTRUMENT EXPIRES AFTER USE | DIM BLUE | |
| BAD INSTRUMENT<br>• NO MORE USES LEFT ON INSTRUMENT<br>• INVALID INSTRUMENT | BLINK F YELLOW/OFF | |
| IN FOLLOWING | BLUE | |
| CAMERA CONTROL | BLUE | |
| GUIDED TOOL CHANGE | • BLINK M. WHITE – READY FOR GTC<br>• WHITE – NOT READY FOR GTC/STERILE ADAPTER PRESENT<br>• BLINK M DIM BLUE/WHITE – INSTRUMENT ENGAGEMENT DELAY<br>• BLINK M DIM BLUE/OFF – SEARCHING FOR C-BALL<br>• BLINK F YELLOW/OFF – INVALID INSTRUMENT | |
| INSTRUMENT/CAMERA ARM CLUTCH | IF INSTRUMENT INSTALLED BLINK M HALF OFF/BLUE HALF BLUE/OFF<br>IF NO INSTRUMENT INSTALLED BLINK M HALF OFF/WHITE HALF WHITE/OFF | |
| ERROR STATE<br>• ARM ASSOCIATED FAULT<br>• UNABLE TO HOME | BLINK F RED/OFF | |
| MATCH GRIPS | | |
| SYSTEM ON BATTERY | BLINK M YELLOW/OFF ALL ARMS | |
| SCOPE ANGLE SELECTION | | |
| INADEQUATE RESERVE POWER (PSC) | BLINK M RED/OFF ALL ARMS | |
| EXCESSIVE FORCE (PSC COLLISION) | | |
| DUAL CONSOLE CONTROL | HALF DIM PURPLE AT ALL TIMES EXCEPT FOLLOWING: PURPLE OTHER HALF IS SAME AS NORMAL ARM FOR ALL OTHER BEHAVIORS INSTRUMENT/CAMERA ARM CLUTCH IS SAME AS NORMAL | |
| SUJ CLUTCH | N/A | |
| MASTER CLUTCH | N/A | |
| COAG/CUT | N/A – COOL BLUE SIZZLE | |

*Fig. 13*

INDICATOR FOR TOOL STATE AND COMMUNICATION IN MULTI-ARM ROBOTIC TELESURGERY

CROSS-REFERENCE TO RELATED APPLICATIONS

This application is a continuation of U.S. patent application Ser. No. 13/599,336, filed Aug. 30, 2012, which is a continuation of U.S. patent application Ser. No. 11/556,484, filed Nov. 3, 2006 and issued as U.S. Pat. No. 8,273,076, which is a continuation-in-part of U.S. patent application Ser. No. 11/478,416, filed Jun. 28, 2006 and issued as U.S. Pat. No. 8,100,133, which claims the benefit of U.S. Provisional Application No. 60/752,755, filed Dec. 20, 2005, the full disclosures of which (including all references incorporated by reference therein) are incorporated by reference herein for all purposes.

The U.S. patent application Ser. No. 11/478,416 also claims the benefit of U.S. Provisional Application No. 60/695,611, filed Jun. 30, 2005, the full disclosure of which (including all references incorporated by reference therein is incorporated by reference herein for all purposes.

TECHNICAL FIELD

The present invention is generally related to medical and/or robotic devices, systems, and methods.

BACKGROUND

Minimally invasive medical techniques are intended to reduce the amount of extraneous tissue which is damaged during diagnostic or surgical procedures, thereby reducing patient recovery time, discomfort, and deleterious side effects. One effect of minimally invasive surgery, for example, may be reduced post-operative hospital recovery times. Because the average hospital stay for a standard surgery is typically significantly longer than the average stay for an analogous minimally invasive surgery, increased use of minimally invasive techniques could save millions of dollars in hospital costs each year. While many of the surgeries performed each year in the United States could potentially be performed in a minimally invasive manner, only a portion of the current surgeries use these advantageous techniques due to limitations in minimally invasive surgical instruments and the additional surgical training involved in mastering them.

Minimally invasive robotic surgical or telesurgical systems have been developed to increase a surgeon's dexterity and to avoid some of the limitations on traditional minimally invasive techniques. In telesurgery, the surgeon uses some form of remote control, e.g., a servomechanism or the like, to manipulate surgical instrument movements, rather than directly holding and moving the instruments by hand. In telesurgery systems, the surgeon can be provided with an image of the surgical site at the surgical workstation. While viewing a two or three dimensional image of the surgical site on a display, the surgeon performs the surgical procedures on the patient by manipulating master control devices, which in turn control motion of the servomechanically operated instruments.

The servomechanism used for telesurgery will often accept input from two master controllers (one for each of the surgeon's hands) and may include two or more robotic arms or manipulators on each of which a surgical instrument is mounted. Operative communication between master controllers and associated robotic arm and instrument assemblies is typically achieved through a control system. The control system typically includes at least one processor which relays input commands from the master controllers to the associated robotic arm and instrument assemblies and back from the instrument and arm assemblies to the associated master controllers in the case of, e.g., force feedback or the like. One example of a robotic surgical system is the DA VINCI® system available from Intuitive Surgical, Inc. of Sunnyvale, Calif.

The roles and interaction among the persons making up a telesurgical team may differ from those of conventional surgery. As telesurgery is often performed in an internal surgical site, at least some of those working under the direction of the lead surgeon (or other robotic system operator) may not have direct access to or direct visualization of the ongoing tissue manipulations. For example, surgical assistants within the operating room may remove a first surgical instrument (such as an electrosurgical scalpel) from a manipulator and replace it with a different surgical instrument (such as a needle holder), as a surgeon may desire the use of different surgical instruments during different phases of a surgical procedure. Similarly, the assistant may reposition a surgical instrument during a procedure, so that rather than approaching the procedure from a first minimally invasive access site, the instrument is advanced toward the internal surgical site from a second, different access site. More complex robotic systems (and team interactions) may also be used. For example, as surgery is often performed with more than two tools, input devices may be provided for one or more additional surgeons, with each additional surgeon robotically controlling (for example) at least one surgical instrument.

While the new telesurgical systems, devices and methods have proven highly effective and advantageous, still further improvements would be desirable. In general, it would be desirable to provide improved robotic and/or surgical devices, systems and methods, particularly for performing telesurgical procedures. It may also be desirable to provide improved techniques for communication among the members of a telesurgical team, and for interfacing with the telesurgical apparatus so as to more fully take advantage of the capabilities of telesurgery to provide enhanced patient outcomes with improved efficiencies. It may be particularly beneficial to avoid unnecessary interruptions and distractions of a surgeon or other system operator, and to avoid delays and/or mistakes in the coordinated activities of a telesurgical team.

SUMMARY

The present invention provides a surgical manipulator assembly and system including an indicator component for providing signals, such as state or identity information. In one embodiment, the invention provides an indicator associated with one or more robotic manipulator assemblies for communication of a state of the manipulator assembly or other component of the robotic system, for identification of one or more particular manipulators, or the like. The indicator(s) can provide an additional user interface between the robotic system and, for example, a surgical assistant, system operator, or the like.

In accordance with an embodiment of the present invention, a surgical manipulator assembly is provided, the assembly comprising a manipulator movably supporting a tool holder; and an indicator section operably coupled to the manipulator for indicating state or identity information, the indicator section including a multiple-color light emitting diode (LED) and a translucent housing.

In accordance with an embodiment of the present invention, another surgical manipulator assembly is provided, the assembly comprising a manipulator movably supporting a tool holder for mounting a tool; and an indicator section operably coupled to the manipulator for indicating state or identity information, the indicator section including a multiple-color light emitting diode (LED), a translucent housing, and a magnet for operably s coupling to a metal tab of a sterile drape used to substantially cover the surgical manipulator assembly from a sterile field.

In accordance with yet another embodiment of the present invention, a robotic surgical manipulator system is provided, the system comprising a manipulator assembly, including a manipulator movably supporting a tool holder, and an indicator section operably coupled to the manipulator for indicating state or identity information, the indicator section including a multiple-color light emitting diode (LED) and a translucent housing. The system further includes a tool mounted on the tool holder, and a processor operably coupled to the manipulator assembly for inducing the LED to indicate state or identity information.

Advantageously, the present invention provides for facilitating communications between the telesurgical system and/or members of a telesurgical team.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIG. 13 is a listing of separately identifiable visual signals which may be generated by the indicator of FIG. 6, along with their associated meanings, in accordance with an embodiment of the present invention.

Figure 1:
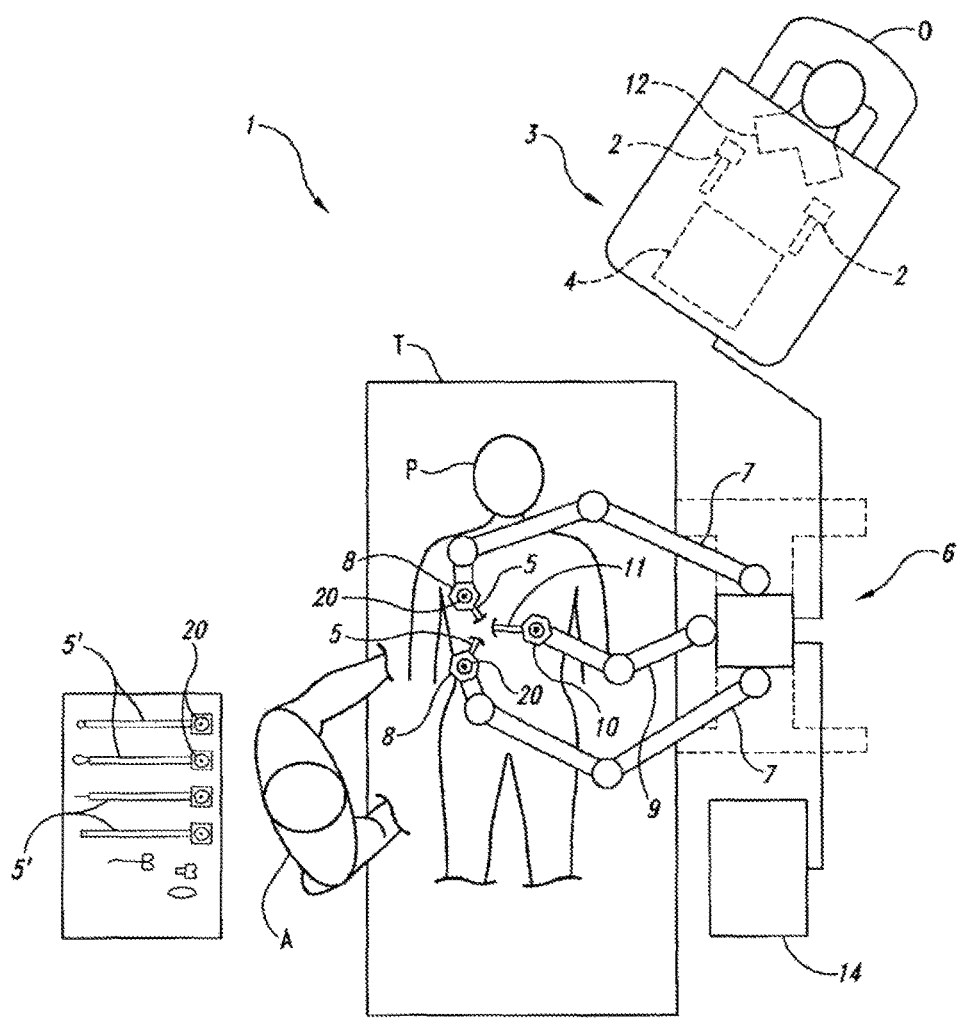
FIG. 1 is a schematic plan view of a portion of an operating theater illustrating a robotic surgical system in use, including a master surgeon console or workstation for inputting a surgical procedure and a robotic manipulator system for robotically moving surgical instruments having surgical end effectors at a surgical site within a patient.

Embodiments of the present invention and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

The present invention generally provides improved robotic and/or medical devices, systems and methods. Embodiments of the present invention are particularly well suited for telesurgery, often providing an additional form of user interface that can enhance communication between a surgical system operator, an assistant, other members of a telesurgical team, and/or the telesurgical system. Other embodiments of the invention may be well suited for use in other telerobotic or robotic environments, particularly with robotic systems having a plurality of manipulators.

Figure 2:
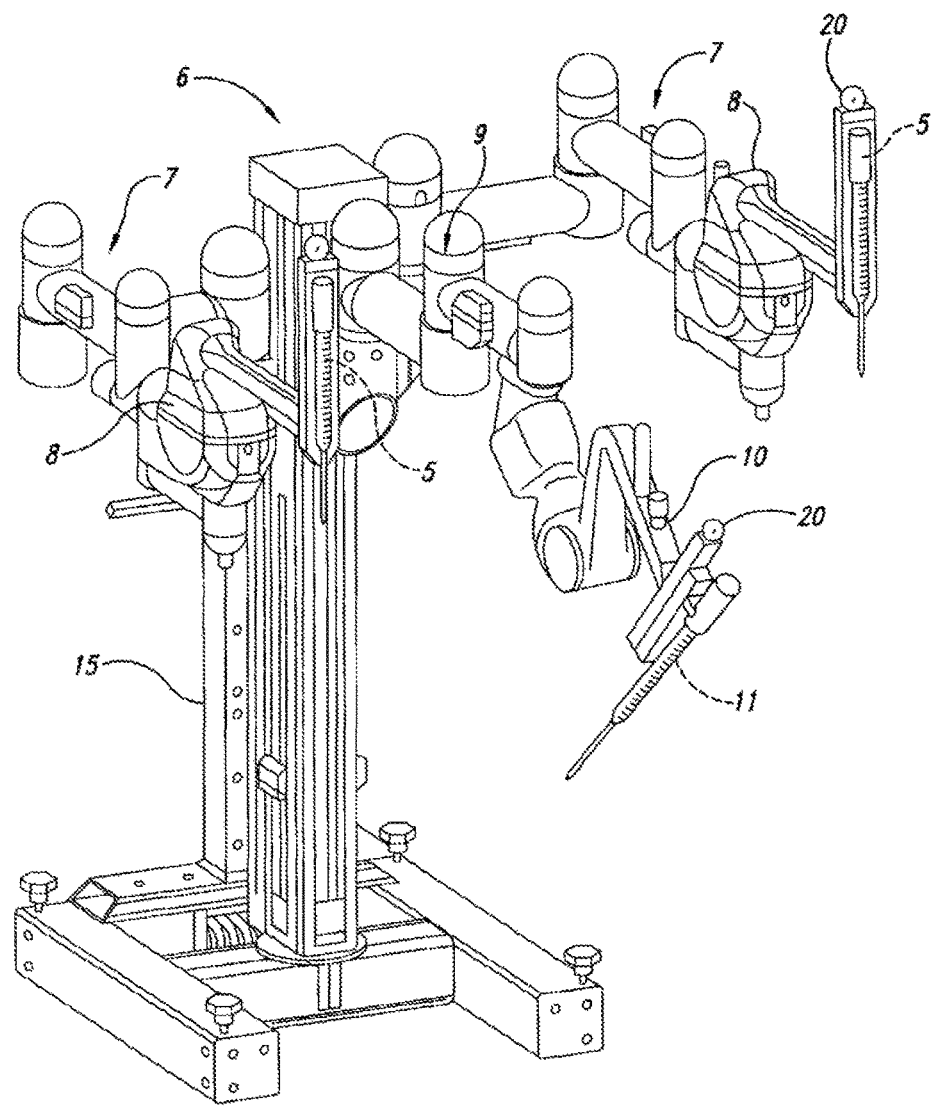
FIG. 2 is a perspective view of an embodiment of a manipulator system, including positioning linkages or set up joints which allow at least two patient side robotic manipulators and one endoscope or camera robotic manipulator to be pre-configured for surgery.
Figure 3:
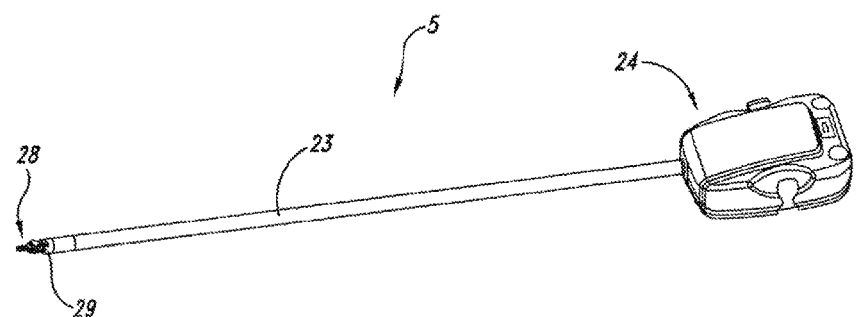
FIG. 3 is a perspective view of an example of an articulated surgical instrument for use in the system of FIG. 1.

FIGS. 1-3 illustrate components of a robotic surgical system 1 for performing minimally invasive robotic surgery. System 1 is similar to that described in more detail in U.S. Pat. No. 6,246,200, the full disclosure of which is incorporated herein by reference. A system operator O (generally a surgeon) performs a minimally invasive surgical procedure on a patient P lying on an operating table T. The system operator O manipulates one or more input devices or masters 2 at a surgeon's console 3. In response to the surgeon's input commands, a computer processor 4 of console 3 directs movement of endoscopic surgical instruments or tools 5, effecting servomechanical movement of the instruments via a robotic patient-side manipulator system 6 (a cart-mounted system in this example).

Typically, manipulator system 6 includes at least 3 robotic manipulator assemblies. Two linkages 7 (mounted at the sides of the cart in this example) support and position manipulators 8 with linkages 7 in general supporting a base of the manipulators 8 at a fixed location during at least a portion of the surgical procedure. Manipulators 8 move surgical tools 5 for robotic manipulation of tissues. One additional linkage 9 (mounted at the center of the cart in this example) supports and positions manipulator 10 which controls the motion of an endoscope/camera probe 11 to capture an image (preferably stereoscopic) of the internal surgical site. The fixable portion of positioning linkages 7, 9 of the patient-side system is sometimes referred to herein as a "set-up arm".

In one example, the image of the internal surgical site is shown to operator O by a stereoscopic display 12 in surgeon's console 3. The internal surgical site is simultaneously shown to assistant A by an assistance display 14. Assistant A assists in pre-positioning manipulator assemblies 8 and 10 relative to patient P using set-up linkage arms 7, 9; in swapping tools 5 from one or more of the surgical manipulators for alternative surgical tools or instruments 5'; in operating related non-robotic medical instruments and equipment; in manually moving a manipulator assembly so that the associated tool accesses the internal surgical site through a different aperture, and the like.

In general terms, the linkages 7, 9 are used primarily during set-up of patient-side system 6, and typically remain in a fixed configuration during at least a portion of a surgical procedure. Manipulators 8, 10 each comprise a driven linkage which is actively articulated under the direction of surgeon's console 3. Although one or more of the joints of the set-up arm may optionally be driven and robotically controlled, at least some of the set-up arm joints may be configured for manual positioning by assistant A.

For convenience, a manipulator such as manipulator 8 that is supporting a surgical tool used to manipulate tissues is sometimes referred to as a patient-side manipulator (PSM), while a manipulator 10 which controls an image capture or data acquisition device such as endoscope 11 may be referred to as an endoscope-camera manipulator (ECM). The manipulators may optionally actuate, maneuver and control a wide variety of instruments, tools, image capture devices, and the like which are useful for surgery.

As can be seen in FIGS. 1 and 2, indicators 20 are disposed on each manipulator assembly. In this embodiment, indicators 20 are disposed on manipulators 8, 10 near the interface between the manipulators and their mounted tools 5. In alternative embodiments, indicators 20 may instead be disposed on set-up joints 7, 9, on tools 5, elsewhere on manipulators 8, 10, or the like, with the indicators preferably being sufficiently close to the tools so that a signal generated by a particular indicator can be readily associated with a particular tool when the signal is viewed by assistant A. In FIG. 1, additional indicators 20 are shown in a rack or other structure supporting additional tools 5', with each indicator again being associated with a particular tool (or type of tool).

As can be seen in FIG. 1, the system operator O is largely immersed in the environment of and interaction with workstation 3. The system operator sees images presented by display 12 and manipulates input devices 2, and in this embodiment, processor 4 correlates the movement of the end effectors of tools 5 so that the images of the end effectors follow the movements of the input devices in the hands of the system operator O.

It can be advantageous to avoid distracting system operator O during a surgical procedure which may shift the operator's attention away from the internal surgical site. Even when assistant A is replacing a tool 5 with an alternative tool 5', the system operator may continue manipulating tissues with another tool, or may want to continue to view the surgical site to monitor bleeding, and/or the like. Nonetheless, it may be difficult for the system operator to communicate clearly with assistant A regarding which tool 5 is to be replaced by an alternate tool. Specifically, as endoscope 11 may be at any convenient orientation, the tool associated with the right hand of system operator O will often not be disposed to the right of the endoscope, particularly as viewed by the assistant.

So as to unambiguously identify a tool 5 to be replaced by assistant A, system operator O may input a command into workstation 3 (such as by pushing a button on the input device 2, actuating a foot peddle, inputting a voice command, or the like) so that indicator 20 on the manipulator assembly associated with the specific tool 5 generates a visually identifiable signal that can be viewed by the assistant. A corresponding graphical indication of the signal may be provided to system operator O in display 12, such as presentation of an appropriate icon, superimposing of text on the surgical site, the use of image processing to superimpose false colors on the image of the appropriate end effector, or the like. In response to the signal on indicator 20, assistant A can remove and replace the identified tool 5.

Figure 6:
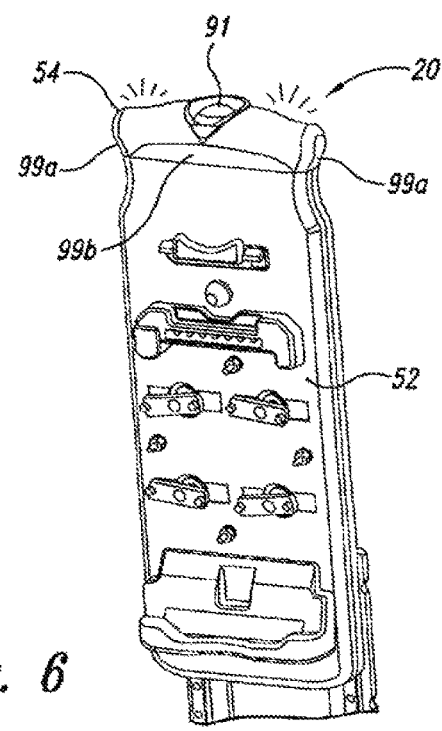
FIG. 6 is a detailed view of an interface portion of the manipulator of FIG. 5, showing a tool holder and adjacent indicator section for outputting visual signals.

There are a number at additional uses for indicators 20 in telesurgical system 1. For example, assistant A will often manually position tools 5 and endoscope 11 when setting up for a surgical procedure, when reconfiguring the manipulator system 6 for a different phase of a surgical procedure, when removing and replacing a tool with an alternate tool 5', and the like. During such manual reconfiguring of the manipulator assembly by assistant A, the manipulator assembly may be placed in a different mode than is used during master/slave telesurgery, with the manually repositionable mode sometimes being referred to as a clutch mode. The manipulator assembly may change between the tissue manipulation mode and the clutch mode in response to an input such as pushing a button or switch on manipulator 8 (or some other component to the manipulator assembly) (e.g., clutch button/switch 91 in FIGS. 6-8) thereby allowing assistant A to change the manipulator mode. By generating appropriate visually identifiable signals with indicators 20 whenever the manipulator is in the clutch mode, assistant A can avoid errors and increase the efficiency of the surgical procedure.

Indicators 20 may also show an associated identifiable signal when, for example, no tool is attached to the manipulator, when a sterile adaptor or interface between tool 5 and manipulator 8 is not properly attached, if an instrument mounted onto a manipulator is incompatible with that manipulator, if the instrument has reached the end of its useful life, and/or the like. For some of these signals, system operator O may initiate generation of the signal and may specify the associated manipulator assembly from which the signal is to be produced. In others, processor 4 may initiate the signal and/or indicate which manipulator assembly is to be indicated. For example, in the case of a power failure, robotic system 1 may continue to operate using backup batteries. So as to indicate to the assistant A that a power failure has occurred, indicators 20 on all manipulators may blink, optionally blinking with a yellow light as a warning. As the power in the battery is drained so that robotic system 1 can no longer continue to provide robotic movement of the tools, all indicators 20 may blink red, thereby indicating a system fault. A wide variety of alternative signals may also be provided, some of which are indicated by the lexicography of FIG. 13.

FIG. 3 illustrates a perspective view of an articulated surgical tool or instrument 5. Tool 5 has a proximal housing 24 which interfaces with a tool holder of the manipulator, generally providing a quick release mounting engagement through a sterile adapter or interface, an example of which is disclosed in U.S. patent application Ser. No. 11/314,040, filed Dec. 20, 2005, and U.S. patent application Ser. No. 11/395,418, filed Mar. 31, 2006, which are incorporated by reference herein for all purposes. Tool 5 includes an elongate shaft 23 supporting an end effector 28 relative to proximal housing 24. Proximal housing 24 accepts and transmits drive signals or drive motion between the manipulator 8 and the end effector 28. An articulated wrist 29 may provide two degrees of freedom of motion between end effector 28 and shaft 23, and the shaft may be rotateable relative to proximal housing 24 about the axis of the shaft so as to provide the end effector 28 with three orientational degrees of freedom within the patient's body.

Figure 4:
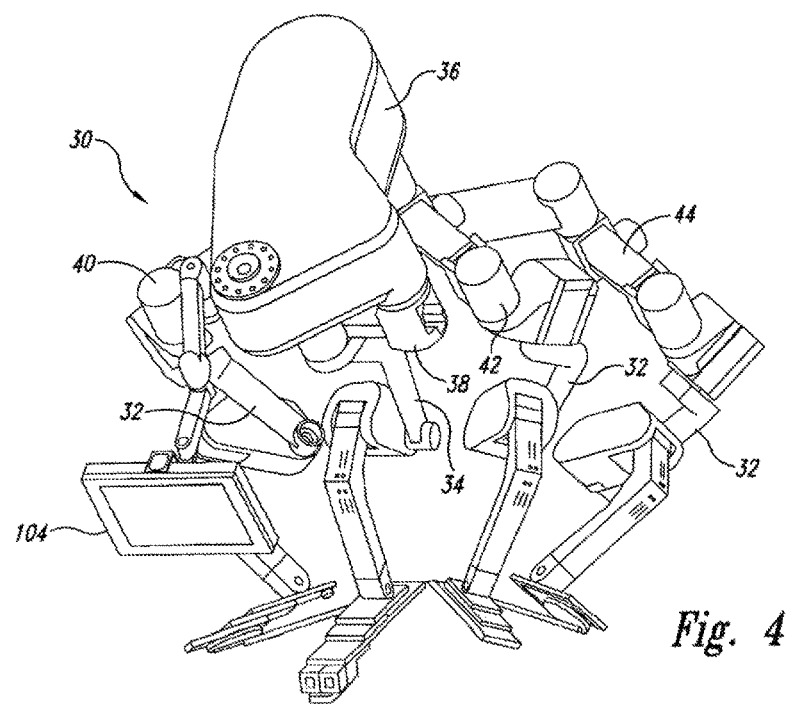
FIG. 4 is a perspective from above of an alternative manipulator system including a plurality of positioning linkages, each supporting a manipulator assembly.

Referring now to FIG. 4, a perspective view is illustrated of an alternative modular manipulator support assembly 30 that may be mounted to a ceiling of an operating room. The modular manipulator support 30 aligns and supports a robotic manipulator system relative to a set of desired surgical incision sites in a patient's body. Modular manipulator support 30 generally includes an orientating platform 36 and a plurality of configurable set-up linkage arms 38, 40, 42, 44 that may be coupled to the orienting platform. Each arm movably supports an associated manipulator 32, 34, which in turn movably supports an associated tool or an image capture device. Orienting platform 36 also supports an assistant display 104, which may be used for set-up, instrument changes, viewing of the procedure and the like. The structures and use of any of the components of modular manipulator support assembly 30 are analogous to those described above regarding manipulator system 6, and are more fully described in co-pending U.S. patent application Ser. No. 11/043,698, filed on Jan. 24, 2005, and entitled "Modulator Manipulator Support For Robotic Surgery", the full disclosure of which is incorporated herein by reference. As generally described above, each manipulator 32, 34 of modular manipulator support 30 may include an indicator 20.

Figure 5:
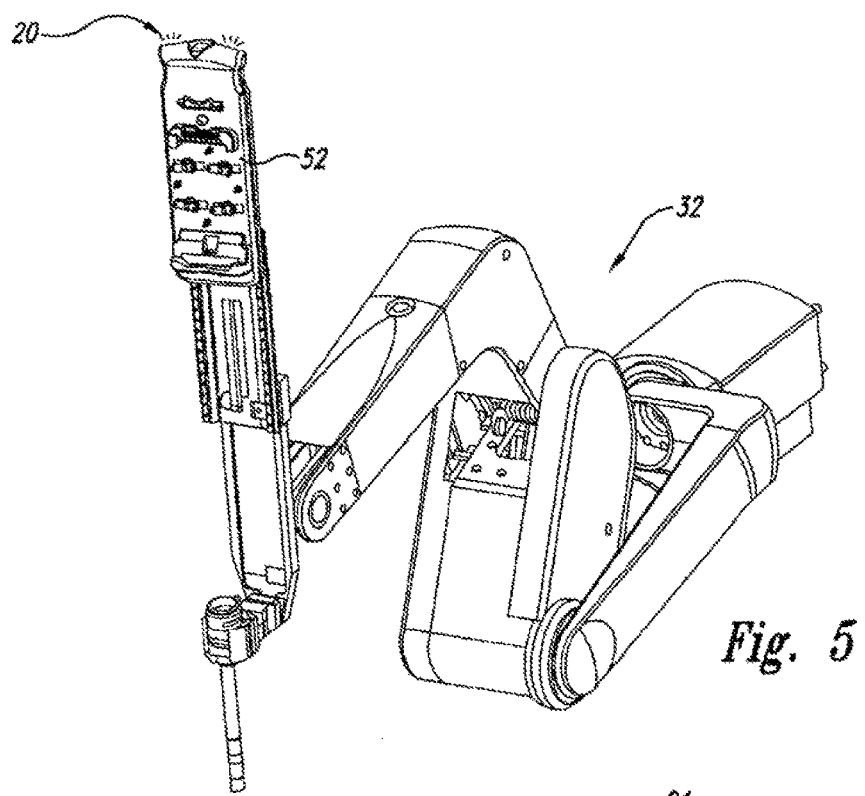
FIG. 5 is a perspective view of a manipulator for use in a manipulator system in accordance with an embodiment of the present invention.
Figure 14:
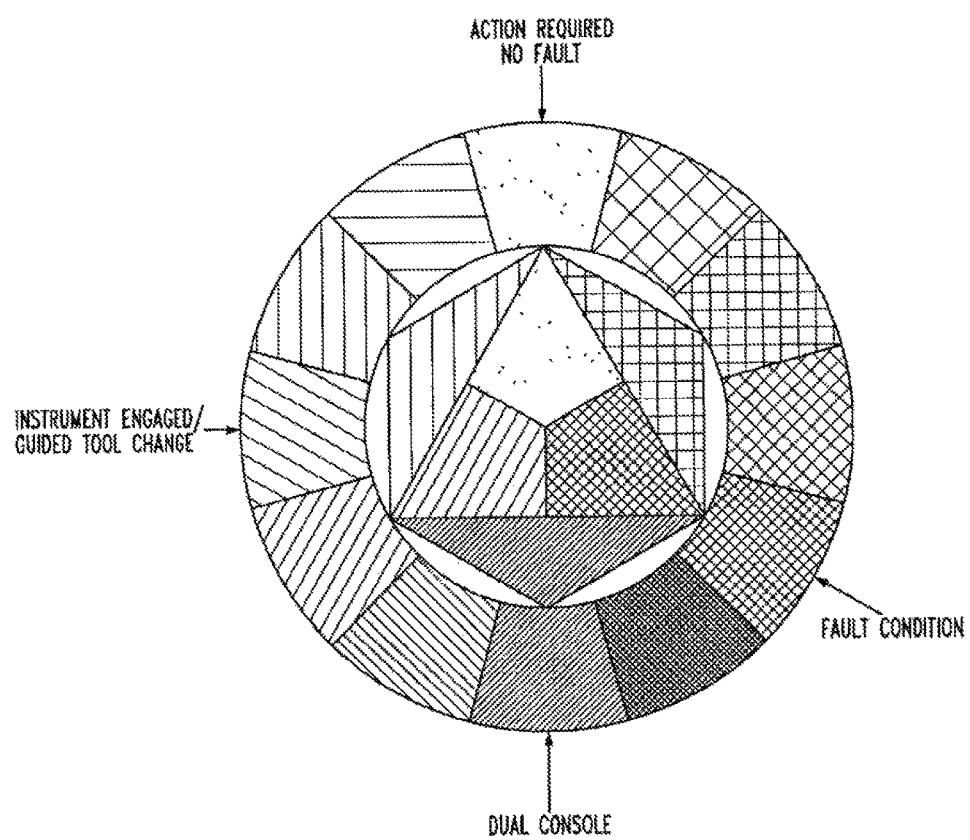
FIG. 14 illustrates colors which can be generated by the indicator of FIG. 6, along with the general meanings of those colors, in accordance with an embodiment of the present invention.

Manipulator 8, 10 is shown in more detail in FIG. 5, which also shows indicator 20 near a tool holder 52. The indicator 20 is shown in more detail in FIG. 6, and in isolation with some of the internal components being schematically shown by dashed lines) in FIGS. 7A-7B and 8A-8B. In one embodiment, the indicator 20 generally comprises a clear and/or translucent polymer body or housing 54 in which a light emitting diode (LED) array 56 is mounted. In this embodiment, a pair of LED arrays 56 are included. LED array 56 includes a red LED, a blue LED, and a yellow LED in one example. In another example, LED array 56 includes a red LED, a green LED, and a blue LED. The LEDs of each array can be independently energized to any of a plurality of illumination or brightness levels, allowing indicator 20 to generate signals in a wide variety of colors, as schematically illustrated in FIG. 14. Additionally, the overall level of illumination from indicator 20 may be varied, and a pattern may be imposed on the cover signal by blinking the illumination on and off, alternating between two different colors, alternating between two different illumination levels, simultaneously displaying two different colors, or the like. The speed of blinking may also be controlled or altered in more complex modulation patterns (with long and short blinks, Morse code, and the like).

As different colors may be combined with different illumination levels and different modulation patterns in a signal, a very large number of independently identifiable signals can be generated, often being more than three separately identifiable signals, typically being more than 10 separately identifiable signals, and optionally being more than 100 separately identifiable signals. Interpretation of the identifiable signals may be facilitated by a list correlating Signals and their meaning, such as that included as FIG. 13 in one example. In some embodiments, a relatively simple signal scheme with a more limited number of signals output by indicator 20 may be combined with supplemental text or graphics output from the assistant display 104 or the like. Hence, the assistant may know that they should look for additional information on the assistant display in response to one or more signals.

So as to facilitate interpretation of the signals generated by indicators 20, a wide variety of signal conventions may be established and/or employed. For example, as can be understood with reference to FIG. 14, signals including the color yellow may generally indicate a warning. Optionally, the manipulator assembly may continue to function while its indicator 20 displays such a yellow warning signal, but the assistant may understand that some action may be advisable. The specific action or meaning of the warning signal may depend on other aspects of the signal, such as other colors being interspersed with a blinking yellow illumination pattern, speed of blinking, or the like. Signals including red may indicate a current or imminent fault that is now or may soon interfere with operation of the manipulator assembly. Green may optionally indicate normal operation is underway, blue may indicate an instrument or a tool is engaged, and/or that a guided tool change is underway or has been requested. Purple may indicate that a second surgeon or system operator is actively controlling the manipulator assembly, or the like. Slow blinking lights may generally indicate a less urgent state than a rapidly blinking indicator 20. Some of these possible conventions are graphically illustrated in FIG. 14.

Figure 7A:
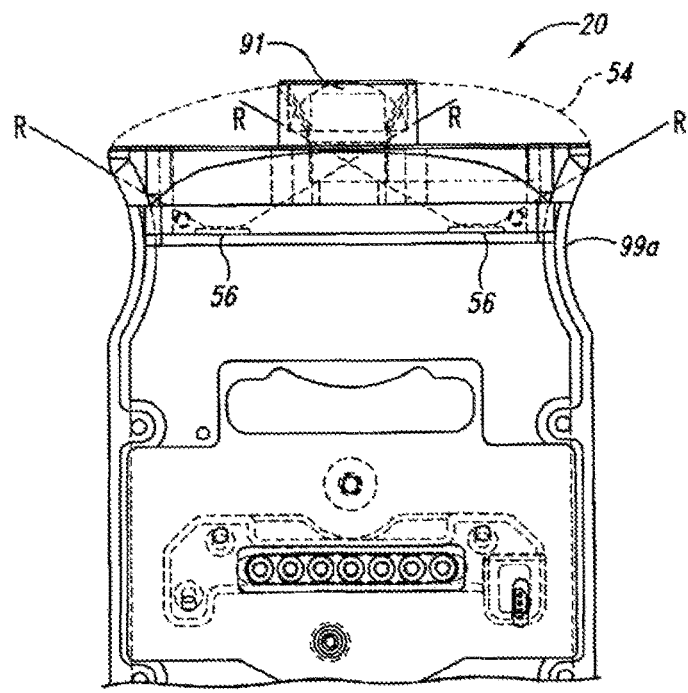
FIGS. 7A and 7B show a front view and a side view, respectively, of the tool holder portion including the indicator and radiation patterns.
Figure 7B:
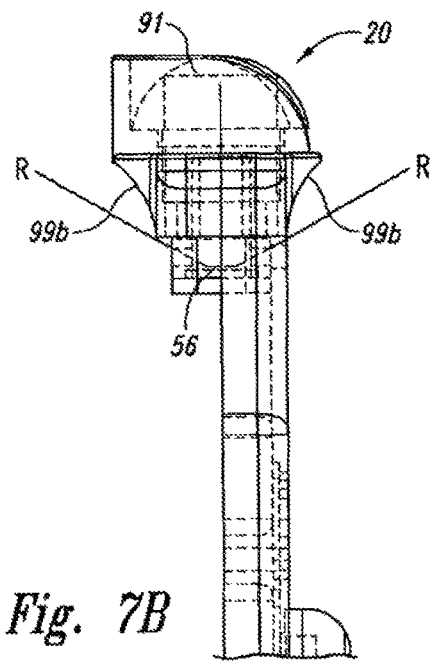

Referring to FIGS. 7A and 7B, a front view and a side view, respectively, of a tool holder portion and indicator section 20 are shown, including examples of radiation patterns emanating from LED arrays 56, shown by lines R. In one example, the 2θ1/2 angle for LED arrays 56 is about 120 degrees. The 2θ1/2 angle is the full viewing angle where the luminous intensity of the LEDs is ½ the intensity of the direct on view. Lines R do not account for the internal reflection in the housing 54, diffusion after internal reflection, and the additional radiation beyond the 2θ1/2 angle boundary. Also illustrated are side grip points 99a and front/back grip points 99b for the user to grip and/or manually move the manipulator while operating clutch button/switch 91.

Figure 8A:
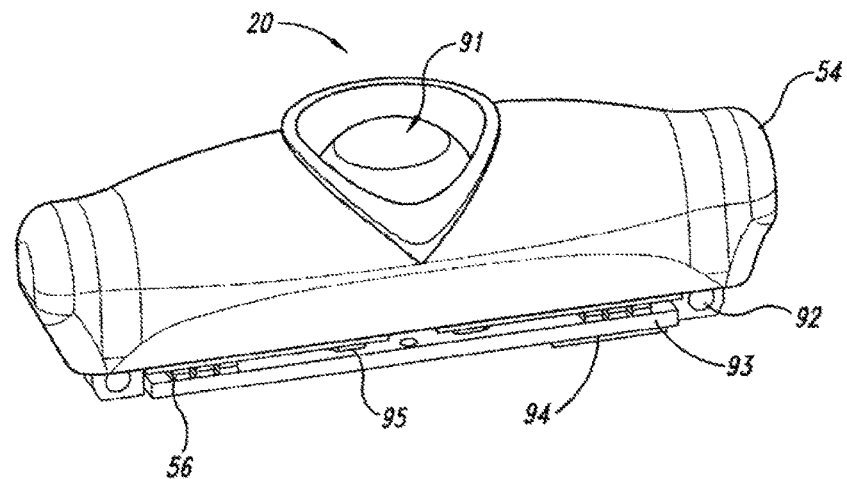
FIGS. 8A and 8B show perspective views of the indicator section in isolation in accordance with an embodiment of the present invention.
Figure 8B:
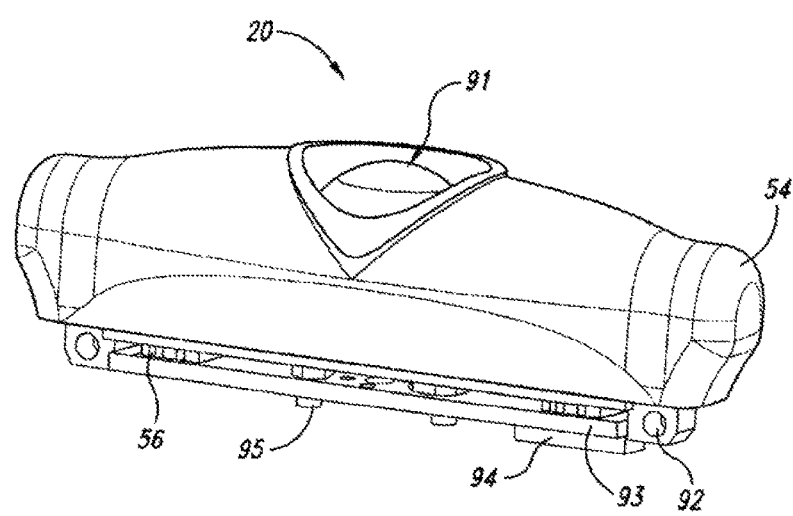

Referring to FIGS. 8A and 8B, indicator section 20 includes clutch button/switch 91, mounting holes 92, a circuit board 93 to which the LE arrays 56 are mounted, an electrical connector 94 (e.g., a flat flexible cable connector), and mounting screws 95 to mount the circuit board 93 to the housing 54.

Figure 9A:
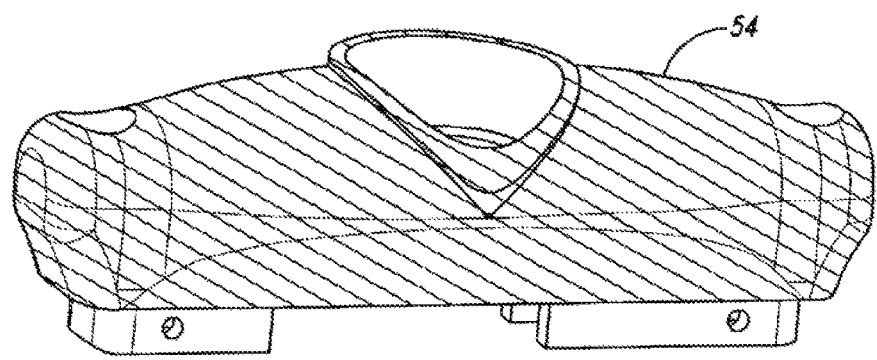
FIGS. 9A and 9B illustrate a surface texture of the indicator section in accordance with an embodiment of the present invention.
Figure 9B:
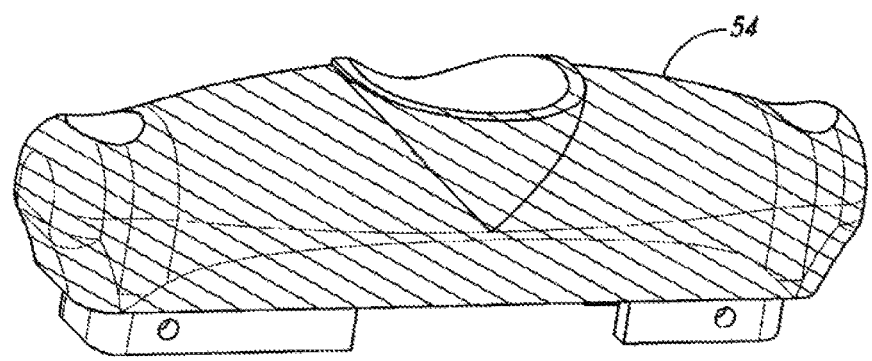

FIGS. 9A and 9B illustrate front and back perspective views of body/housing 54, In one embodiment, housing 54 is comprised of polycarbonate or similar clear plastic with an acceptable or compliant UL flame rating. In yet another embodiment, the exterior surface of housing 54 is relatively rough or frosted, thereby providing for increased dispersion of light, and the interior surface of housing 54 is relatively smooth or polished, thereby allowing for better transmittance of the dispersed light. The hashed lines in FIGS. 9A and 9B illustrate the frosted exterior surface of housing 54.

Figure 10:
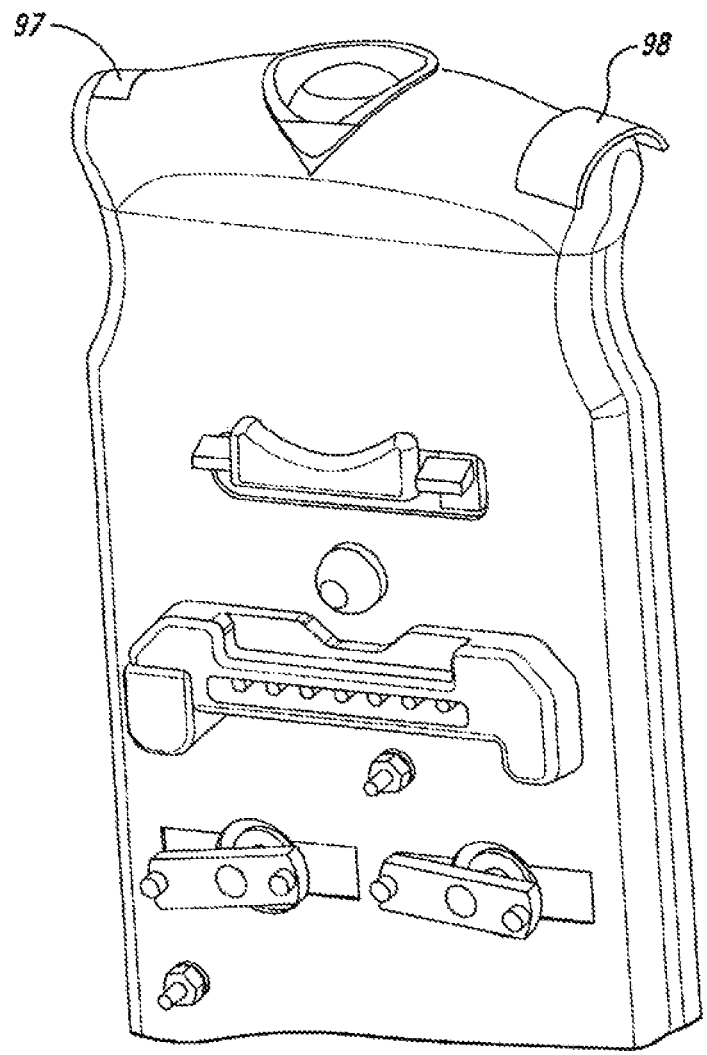
FIG. 10 illustrates the indicator section including a magnet for operably coupling to a metal tab in accordance with an embodiment of the present invention.

FIG. 10 illustrates an optional magnet 97 included in indicator section 20 and a metal strip 98 that is part of a sterile drape (not shown) used to aid in substantially covering the manipulator, assembly, and system of the present invention to maintain a sterile field. An example of a sterile drape is disclosed in U.S. application Ser. No. 11/240,113, filed Sep. 30, 2005, the full disclosure of which is incorporated herein by reference. Magnet 97 operably couples to metal strip 98 to controllably hold the drape portion to the indicator section and the manipulator, thereby allowing for management of drape material (in particular for keeping excess drape material from obstructing instrument engagements). In one example, magnet 97 may be press fit and/or glued onto the indicator section. Alternatively, metal strip 98 and magnet 97 may be switched such that a magnet, as a part of the sterile drape, and a metal portion, as a part of the indicator section, may be operably coupled to aid in substantially covering the manipulator, assembly, and system of the present invention to maintain a sterile field.

Figure 11:
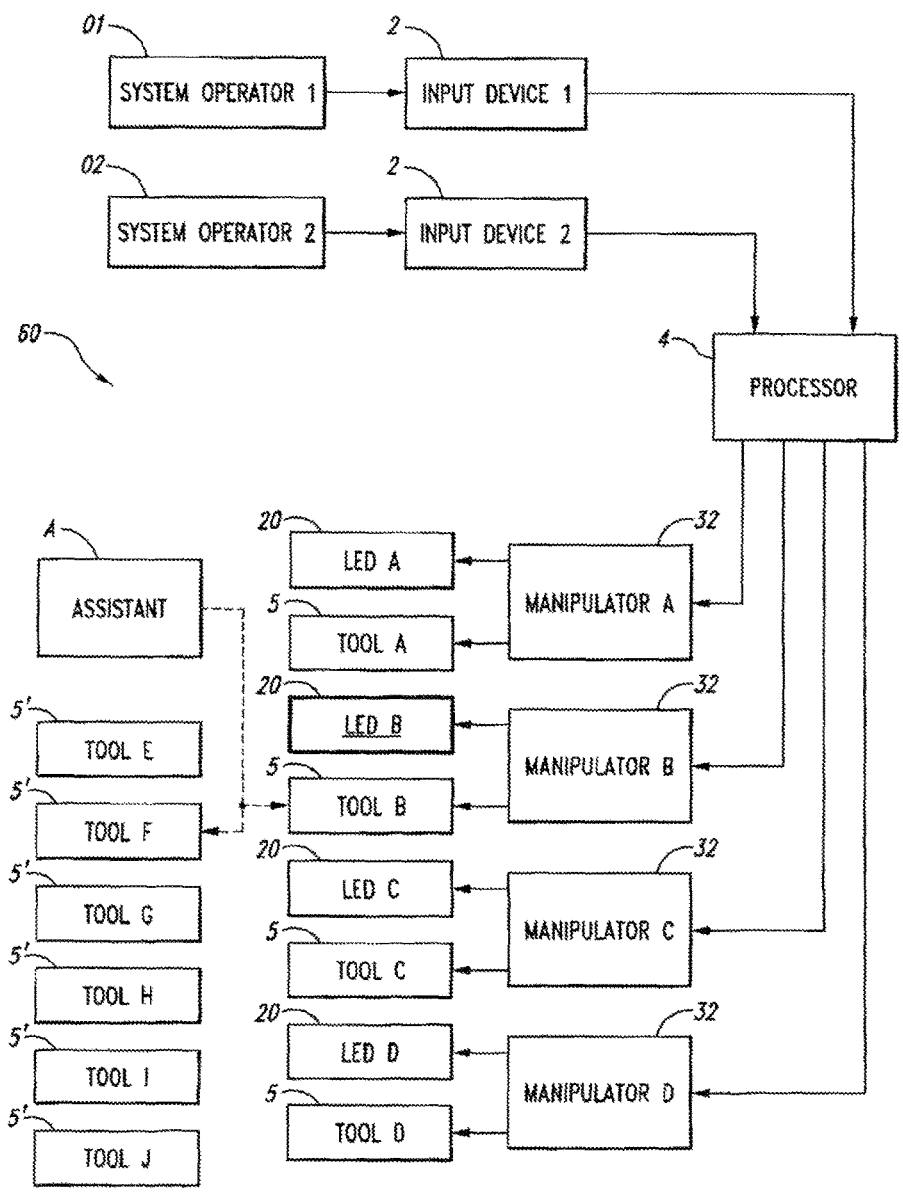
FIG. 11 is a schematic block diagram of an embodiment of an alternative robotic system and method for its use by a plurality of system operators.

Referring now to FIG. 11, a schematic block diagram of a somewhat more complex system 60 is provided. Cooperative telesurgical systems which may be modified to take advantage of the additional user interface provided by indicators 20 is described in more detail in U.S. Pat. No. 6,659,939, the full disclosure of which is incorporated herein by reference. In the system of FIG. 11, a first system operator O1 provides input to a first input device 2. Processor 4 selectively couples the movement commands from the first input device 2 to any of a plurality of manipulator assemblies, for example, to manipulator A and manipulator D. A second system operator O2 inputs movement commands to a second input device 2 so as to effect movement of a manipulator 8 manipulator assembly B.

When the second system operator O2 desires the tool 5 attached to manipulator assembly B be replaced by an alternate tool 5', for example, tool F, the system operator may verbally instruct assistant A to mount tool F to his manipulator assembly. The indicator 20 of manipulator assembly B generates a signal in response to an appropriate input by the second system operator O2, clearly indicating to the assistant A which tool from which manipulator assembly is to be replaced. As noted above, additional indicators may optionally be associated with each of the alternative tools 5', thereby foregoing any need for verbal instruction to the assistant regarding which alternative tool is to be mounted to the manipulator.

Processor 4 will typically include data processing hardware and software, with the software typically comprising machine-readable code. The machine-readable code will embody software programming instructions to implement some or all of the methods described herein. While processor 4 is shown as a single block in the simplified schematic of FIG. 11, the processor may comprise a number of data processing circuits, with at least a portion of the processing optionally being performed adjacent input device 1, a portion being performed adjacent manipulator B, and the like. Any of a wide variety of centralized or distributed data processing architectures may be employed. Similarly, the programming code may be implemented as a number of separate programs or subroutines, or may be integrated into a number of other aspects of the robotic systems described herein.

Figure 12:
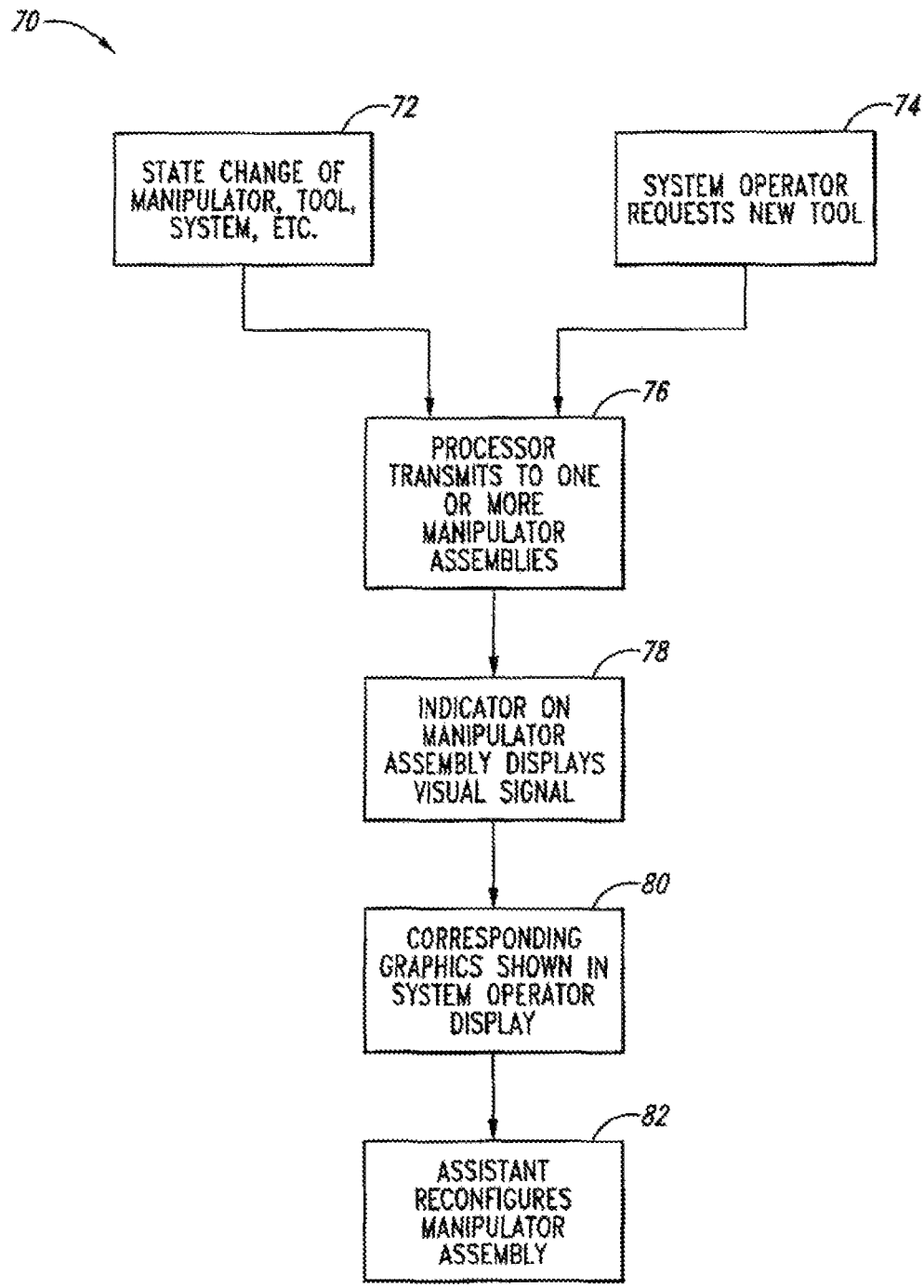
FIG. 12 is a flow chart schematically describing a method for reconfiguring a manipulator assembly in response to an identifiable signal from an associated indicator.

Referring now to FIG. 12, a flowchart 70 schematically illustrates a method for implementing an embodiment of the present invention. The method 70 may begin with a change in state of the manipulator, tool, system, or the like at a step 72. For example, an assistant may actuate a clutch mode button on the manipulator, the tool may reach the end of its useful life, a manipulator fault may be detected, or the like. In other embodiments, the system operator may initiate method 70 by requesting a new tool at a step 74, or in some other manner indicating which of one or more manipulator assemblies is to generate a signal to be perceived by an assistant or some other person.

Regardless of whether the signal is initiated by a change in state or a system operator, the processor will typically transmit an appropriate command to one or more of the manipulator assemblies at a step 76, and, in response, the indicator on that manipulator assembly will display a visual signal at a step 78. Optionally, corresponding graphics may be shown in a system operator display at a step 80, thereby allowing the system operator to maintain his or her concentration on the internal surgical site.

In response to the visual signal, the other person, such as an assistant, may optionally reconfigure the manipulator assembly at a step 82. For example, the assistant may remove and replace a tool (with its end effector) or may manually reposition the manipulator linkage so as to move the end effector into a desired position. In some embodiments, the assistant may merely monitor the manipulator assembly in response to one or more visual signals, and may optionally prepare to take some appropriate action if the visual signal changes so as to indicate that such an action is appropriate.

Embodiments described above illustrate but do not limit the invention. It should also be understood that numerous modifications and variations are possible in accordance with the principles of the present invention. For example, the number of LEDs may vary. Accordingly, the scope of the invention is defined only by the following claims.

We claim:

1. A method comprising:
   receiving an input at a control system indicating a status change for a first tool coupled to a first manipulator assembly of a telesurgical system, wherein the status change is correlated to a procedure to decouple the first tool from the first manipulator assembly or manually reconfigure the first manipulator assembly;
   transmitting a command to the first manipulator assembly; and
   responsive to the transmitted command, activating a multiple-color light emitting diode (LED) array in an indicator section on the first manipulator assembly to generate a signal indicating a reconfiguration action for the first tool or the first manipulator assembly to a first user.

2. The method of claim 1 wherein the input at the control system is received from an input device operated by a second user.

3. The method of claim 1 wherein the input at the control system is received in response to an end-of-life signal from the first tool.

4. The method of claim 1 wherein the input at the control system is received in response to actuation of a manipulator clutch switch on the first manipulator assembly.

5. The method of claim 4 wherein the manipulator clutch switch is changeable between a clutch mode in which the LED array generates a first visually identifiable signal and a manipulation mode in which the LED array generates a second visually identifiable signal.

6. The method of claim 1 wherein the telesurgical system includes a plurality of manipulator assemblies, including the first manipulator assembly.

7. The method of claim 1 further comprising activating the multiple-color light emitting diode (LED) array in the indicator section on the first manipulator assembly to generate a signal identifying a second tool to be coupled to the first manipulator assembly after removal of the first tool from the first manipulator assembly.

8. The method of claim 1, wherein the multiple-color LED array is a tri-colored LED array capable of displaying red, green, and blue.

9. The method of claim 1, wherein the multiple-color LED array in the indicator section on the first manipulator assembly further generates a signal consisting of an identity of the coupled first tool.

10. A method of operating a telesurgical manipulator system, comprising:
receiving an input at a control system to initiate a tool change procedure for a first tool coupled to a first manipulator assembly of the telesurgical manipulator system, wherein the telesurgical manipulator system includes a plurality of manipulator assemblies including the first manipulator assembly;
transmitting a command to the first manipulator assembly of the plurality of manipulator assemblies; and
responsive to the transmitted command, activating a multiple-color light emitting diode (LED) array in an indicator section on the first manipulator assembly to generate a visual signal viewable by a first user, the visual signal correlated with a procedure to decouple the first tool from the first manipulator assembly.

11. The method of claim 10 wherein the input at the control system is received from an input device operated by a second user.

12. The method of claim 10 wherein the input at the control system is received in response to an end-of-life signal from the first tool.

13. The method of claim 10, wherein the multiple-color LED array is a tri-colored LED array capable of displaying red, green, and blue.

14. The method of claim 10 further comprising activating the multiple-color LED array in the indicator section on the first manipulator assembly to generate a signal identifying a second tool to be coupled to the first manipulator assembly after removal of the first tool from the first manipulator assembly.

15. The method of claim 10, wherein the multiple-color LED array in the indicator section on the first manipulator assembly further generates a signal consisting of an identity of the coupled first tool.

16. A method comprising:
receiving an input at a control system for moving a manipulator assembly of a telesurgical system in a manipulation mode;
providing a multiple-color light emitting diode (LED) array in an indicator section on the manipulator assembly;
activating the multiple color LED array to generate a first signal in a first color indicating that the manipulator assembly is in the manipulation mode;
receiving an input at a control system to transition the manipulator assembly from the manipulation mode to a repositioning mode; and
activating the multiple color LED array to generate a second signal in a second color when the manipulator assembly is in the repositioning mode.

17. The method of claim 16 wherein the input at the control system is received in response to actuation of a manipulator clutch switch on the manipulator assembly.

18. The method of claim 17, wherein the first color is different from the second color.

19. The method of claim 16, wherein the multiple-color LED array is a tri-colored LED array capable of displaying red, green, and blue.

* * * * *